(12) United States Patent
Nakada

(10) Patent No.: US 7,155,269 B2
(45) Date of Patent: Dec. 26, 2006

(54) STRESS EVALUATION APPARATUS

(75) Inventor: Masato Nakada, Schaumburg, IL (US)

(73) Assignee: Tanita Corporation, Tokyo (JP)

( * ) Notice: Subject to any disclaimer, the term of this patent is extended or adjusted under 35 U.S.C. 154(b) by 125 days.

(21) Appl. No.: 11/076,947

(22) Filed: Mar. 11, 2005

(65) Prior Publication Data
US 2006/0206022 A1 Sep. 14, 2006

(51) Int. Cl.
A61B 5/05 (2006.01)
A61B 5/00 (2006.01)
(52) U.S. Cl. .................. 600/361; 600/547; 600/366
(58) Field of Classification Search ........... 600/547, 600/306, 309, 506, 345–366
See application file for complete search history.

(56) References Cited
U.S. PATENT DOCUMENTS
5,820,548 A * 10/1998 Sieben et al. ............ 600/361

2005/0101841 A9* 5/2005 Kaylor et al. ............ 600/300
2005/0203435 A1* 9/2005 Nakada .................... 600/547

FOREIGN PATENT DOCUMENTS
JP       07-231880     9/1995
JP       10-005193     1/1998
JP       2003-019122   1/2003

* cited by examiner

Primary Examiner—Charles A. Marmor, II
Assistant Examiner—Navin Natnithithadha
(74) Attorney, Agent, or Firm—McDermott Will & Emery LLP

(57) ABSTRACT

A stress evaluation apparatus includes an impedance measuring unit for measuring an impedance of a fluid discharged from a living body; a temperature measuring unit for measuring a temperature of the fluid discharged from the living body; a pH calculating unit for calculating a pH value based on the impedance and temperature of the fluid discharged from the living body; and a stress evaluating unit for evaluating a stress based on the pH value calculated by the pH calculating unit.

13 Claims, 6 Drawing Sheets

FIG. 1A
FIG. 1B
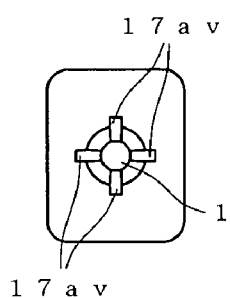
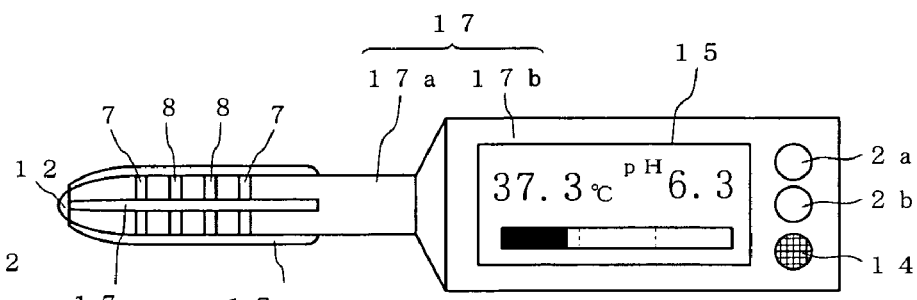

F I G. 4
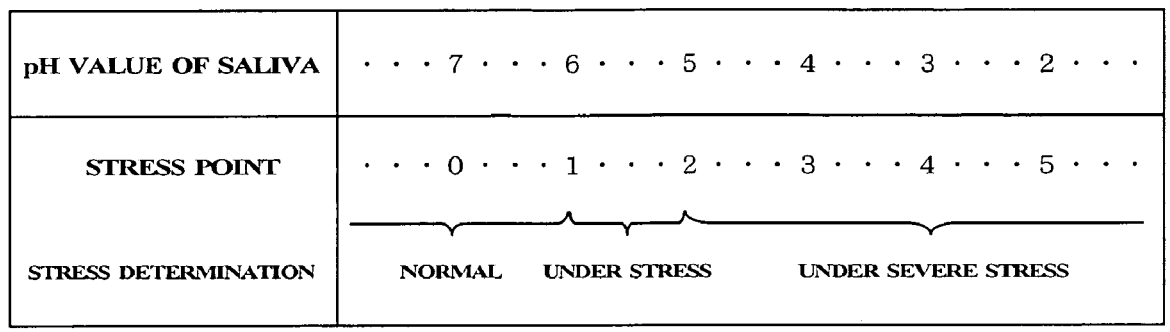

STRESS EVALUATION APPARATUS

FIELD OF THE INVENTION

The present invention relates to a stress evaluation apparatus for evaluating a stress on a living body based on a pH value yielded by impedance measurement of a fluid discharged (secreted or excreted) from the living body.

DESCRIPTION OF THE RELATED ART

In the description of the present invention, stress means the state of a certain reaction (mental distress (anxiety, tension, displeasure, anger, jitters, lethargy, etc.) or physical distress (memory loss, languor, fatigue, anorexia, insomnia, dull headache, headache, stiff neck, etc.) caused in a living body in reaction to an external stimulus caused by its physical environment (temperature, ambient noise, earthquake, etc.), social and cultural concerns (economic crisis, political change, etc.), environmental conditions of individuals (change of abode, transfer of schools, job transfer, retirement, etc.), disunion or conflict in human relationship, or biotic factors (extreme fatigue, injury, physical disease, etc.)

Human beings living in modern society suffer a variety of stresses to accommodate themselves to things or information, which stress is increased by fast-moving technical innovation, or to cope with their jobs, household chores, child care, examinations, and so on. Devices for evaluating stress, which help individuals maintain their physical and mental health in the face of external stimuli they constantly receive, have been disclosed in recent years. For example, Japanese Unexamined Patent Application Publication No. 7-231880 discloses a device for evaluating stress based on RR intervals yielded by an electrocardiogram. Japanese Unexamined Patent Application Publication No. 2003-19122 discloses a device for determining a stress level based on impedance corresponding to stimulus provided when current is applied to electrodes attached to the living body.

However, with the stress evaluation devices described above, the electrodes must be attached to predetermined positions each time the measurement is performed. In addition, the stress evaluation devices cause physical discomfort because of the electrodes attached to the predetermined positions on the living body.

SUMMARY OF THE INVENTION

Accordingly, in order to resolve the problems described above, an aspect of the present invention is to provide a stress evaluation apparatus capable of evaluating a stress on a living body without causing physical discomfort.

The present invention provides a stress evaluation apparatus including an impedance measuring unit for measuring an impedance of a fluid discharged from a living body; a pH calculating unit for calculating a pH value based on the impedance of the fluid discharged from the living body, the impedance being measured by the impedance measuring unit; and a stress evaluating unit for evaluating a stress based on the pH value calculated by the pH calculating unit.

In another aspect of the present invention, the stress evaluation apparatus includes a temperature measuring unit for measuring a temperature of the fluid discharged from the living body. The pH calculating unit calculates the pH value based on the impedance of the fluid discharged from the living body, the impedance being measured by the impedance measuring unit, and the temperature of the fluid discharged from the living body, the temperature being measured by the temperature measuring unit.

In another aspect of the present invention, the stress evaluation apparatus includes a measurement determination processing unit for determining whether the impedance measuring unit measures the impedance of the fluid discharged from the living body. If the impedance measuring unit does not measure the impedance of the fluid discharged from the living body, the measurement determination processing unit indicates that the impedance measuring unit has not measured the impedance of the fluid discharged from the living body.

In another aspect of the present invention, the impedance measuring unit includes a constant current generating unit for generating an alternating-current constant current; a reference resistance through which the alternating-current constant current generated by the constant current generating unit passes; a pair of current supply electrodes for applying the alternating-current constant current from the reference resistance to the fluid discharged from the living body; a pair of voltage detection electrodes for detecting a voltage generated in the fluid discharged from the living body when the pair of current supply electrodes applies the alternating-current constant current to the fluid discharged from the living body; a switch for switching a connection to either both ends of the reference resistance or both electrodes of the pair of voltage detection electrodes; and a converting unit for impedance calculation, for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body. The converting unit divides the voltage generated at both ends of the reference resistance into a real part and an imaginary part. The measurement determination processing unit determines whether the impedance measuring unit has measured the impedance of the fluid discharged from the living body based on the real part and the imaginary part.

In another aspect of the present invention, the stress evaluation apparatus includes a measurement-state determination processing unit for determining whether the state in which the impedance measuring unit measures the impedance of the fluid discharged from the living body is good. If the state in which the impedance measuring unit measures the impedance of the fluid discharged from the living body is not good, the measurement-state determination processing unit indicates that the state in which the impedance measuring unit measures the impedance of the fluid discharged from the living body is not good.

In another aspect of the present invention, the impedance measuring unit includes a constant current generating unit for generating an alternating-current constant current; a reference resistance through which the alternating-current constant current generated by the constant current generating unit passes; a pair of current supply electrodes for applying the alternating-current constant current from the reference resistance to the fluid discharged from the living body; a pair of voltage detection electrodes for detecting a voltage generated in the fluid discharged from the living body when the pair of current supply electrodes applies the alternating-current constant current to the fluid discharged from the living body; a switch for switching a connection to either both ends of the reference resistance or both electrodes of the pair of voltage detection electrodes; and a converting unit for impedance calculation for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body. The measurement-state determination processing unit determines whether the state in which the impedance measuring unit measures the impedance of the fluid discharged from the living body is good, based on the contact impedance calculated by the converting unit and a predetermined threshold that is affected by the contact impedance.

In another aspect of the present invention, the stress evaluation apparatus includes a clock unit for measuring an elapsed time of measurement; and an elapsed-time determination processing unit for determining whether the elapsed time for the measurement measured by the clock unit exceeds one minute if the measurement-state determination processing unit determines that the state in which the impedance measuring unit measures the impedance of the fluid discharged from the living body is not good. The elapsed-time determination processing unit indicates that the elapsed time for the measurement exceeds one minute if the elapsed time for the measurement exceeds one minute, and causes the impedance measuring unit to perform the measurement if the elapsed time for the measurement does not exceed one minute.

In another aspect of the present invention, the impedance measuring unit includes a constant current generating unit for generating an alternating-current constant current; a reference resistance through which the alternating-current constant current generated by the constant current generating unit passes; a pair of current supply electrodes for applying the alternating-current constant current from the reference resistance to the fluid discharged from the living body; a pair of voltage detection electrodes for detecting a voltage generated in the fluid discharged from the living body when the pair of current supply electrodes applies the alternating-current constant current to the fluid discharged from the living body; a switch for switching a connection to either both ends of the reference resistance or both electrodes of the pair of voltage detection electrodes; and a converting unit for impedance calculation for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body.

In one aspect of the present invention, the fluid discharged from the living body is saliva.

In another aspect of the present invention, the fluid discharged from the living body is urine.

In an aspect of the present invention, wherein the fluid discharged from the living body is saliva, the stress evaluation apparatus has a bar capable of being put into the mouth of the living body, the bar having the pair of current supply electrodes, the pair of voltage detection electrodes, and projections formed so as to be in contact with the pair of current supply electrodes and the pair of voltage detection electrodes, wherein the pair of current supply electrodes, the pair of voltage detection electrodes, and the projections are formed on the periphery of the bar.

In another aspect of the present invention, wherein the fluid discharged from the living body is saliva, the stress evaluation apparatus has a bar capable of being put into the mouth of the living body. The bar has the pair of current supply electrodes, the pair of voltage detection electrodes, and grooves in contact with the pair of current supply electrodes and the pair of voltage detection electrodes. The pair of current supply electrodes, the pair of voltage detection electrodes, and the grooves are formed on the periphery of the bar.

In a further aspect of the present invention, the grooves are formed such that their width gradually increases from the side of the bar put into the mouth of the living body.

Since the stress evaluation apparatus of the present invention evaluates stress based on the measured impedance of fluid discharged from a living body, it avoids the trouble of mounting electrodes at predetermined positions on the living body and eliminates the physical discomfort caused by the electrodes being mounted on the predetermined positions on the living body.

Since the stress evaluation apparatus of the present invention calculates the pH value based on the impedance and temperature of fluid discharged from the living body, the effect of the impedance varying with the temperature of the fluid discharged from the living body is offset, thus easily yielding results with high accuracy.

The stress evaluation apparatus of the present invention indicates that the impedance measuring unit has not measured the impedance of the fluid discharged from the living body if the measurement determination processing unit determines that the impedance measuring unit has not measured the impedance of the fluid discharged from the living body. The measurement determination processing unit determines whether the impedance measuring unit has measured the impedance of the fluid discharged from the living body based on the imaginary part and the real part of the voltage generated at both ends of the reference resistance. Accordingly, the inventive stress evaluation apparatus is user friendly.

The stress evaluation apparatus of the present invention indicates that the state in which the impedance measuring unit measures the impedance of the fluid discharged from the living body is not good if the measurement-state determination processing unit determines that the state in which the impedance measuring unit measures the impedance of the fluid discharged from the living body is not good. The measurement-state determination processing unit determines whether the state in which the impedance measuring unit measures the impedance of the fluid discharged from the living body is good based on the contact impedance and the threshold. Accordingly, the stress evaluation apparatus is user friendly.

The stress evaluation apparatus of the present invention is user friendly because it indicates that the elapsed time for the measurement has exceeded one minute if the elapsed-time determination processing unit determines that the elapsed time for the measurement exceeds one minute. The elapsed-time determination processing unit causes the impedance measuring unit to perform the measurement again if the elapsed time for the measurement is less than one minute. Accordingly, the present invention correctly yields a sufficient amount of measurement data.

In the stress evaluation apparatus of the present invention, the converting unit for impedance calculation calculates the overall impedance, the temporary impedance of the fluid discharged from the living body, the contact impedance, and the impedance of the fluid discharged from the living body based on the voltage detected when a connection is switched to both ends of the reference resistance and the voltage detected when the connection is switched to both electrodes of the pair of voltage detection electrodes. Accordingly, the present invention easily yields results with high accuracy.

Since the stress evaluation apparatus of the present invention measures saliva as the fluid discharged from the living body, it alleviates trouble and eliminates physical discomfort.

Since the stress evaluation apparatus of the present invention measures urine as the fluid discharged from the living body, it alleviates trouble and eliminates physical discomfort.

Since the stress evaluation apparatus of the present invention has projections on the periphery of a bar, the saliva in the mouth of the living body is carried on the projections due to capillary action and is in positive contact with the electrodes, thus easily yielding measurement data with high accuracy.

Since the stress evaluation apparatus of the present invention has grooves on the periphery of the bar thereof, the saliva in the mouth of the living body is carried in the grooves due to capillary action and is in positive contact with the electrodes, thus easily yielding measurement data with high accuracy.

Since the stress evaluation apparatus of the present invention is formed such that the width of the grooves is gradually increased from the side put into the mouth of the living body, saliva carried in the grooves due to capillary action is prevented from spilling over the user's mouth.

BRIEF DESCRIPTION OF THE DRAWINGS

FIG. 1A is an outside view of a stress evaluation apparatus according to an embodiment of the present invention, viewed from the side put into the mouth of a living body;

FIG. 1B is an outside view of the stress evaluation apparatus in FIG. 1A, viewed from the side of an indicator (the front face of a holder);

FIG. 4 is a table illustrating stress evaluation criteria;

DETAILED DESCRIPTION OF THE INVENTION

Figure 2:
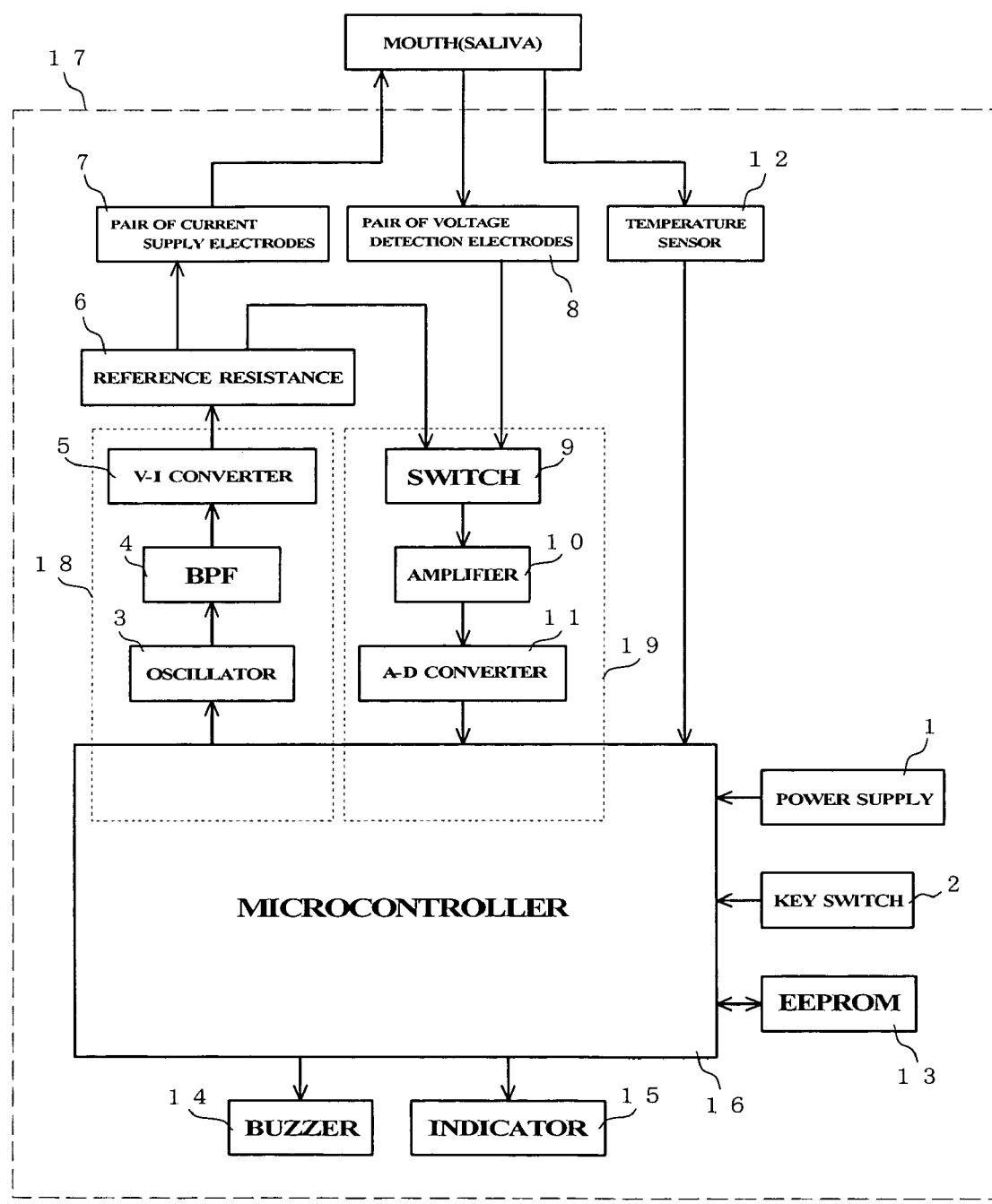
FIG. 2 is a block diagram of a stress evaluation apparatus according to an embodiment of the present invention.

A stress evaluation apparatus according to the present invention includes an impedance measuring unit, a measurement determination processing unit, a measurement-state determination processing unit, a clock unit, an elapsed-time determination processing unit, a temperature measuring unit, a pH calculating unit, and a stress evaluating unit.

The impedance measuring unit measures an impedance of a fluid (for example, saliva or urine) discharged (secreted or excreted) from a living body in a conventional manner.

The measurement determination processing unit determines whether the impedance measuring unit has measured the impedance of the fluid discharged from the living body. If the impedance measuring unit does not measure the impedance of the fluid discharged from the living body, the measurement determination processing unit indicates that the impedance measuring unit has not measured the impedance of the fluid discharged from the living body.

The measurement-state determination processing unit determines whether the state in which the impedance measuring unit measures the impedance of the fluid discharged from the living body is good. If the measurement state is not good, the measurement-state determination processing unit indicates that the measurement state is not good.

The clock unit measures an elapsed time for the measurement.

The elapsed-time determination processing unit determines whether the elapsed time for the measurement, measured by the clock unit, exceeds a predetermined time (for example, one minute) if the measurement-state determination processing unit determines that the state in which the impedance measuring unit measures the impedance of the fluid discharged from the living body is not good. If the elapsed time exceeds the predetermined time, the elapsed-time determination processing unit indicates that the elapsed time exceeds the predetermined time. If the elapsed time does not exceed the predetermined time, the elapsed-time determination processing unit causes the impedance measuring unit to perform the measurement again.

The temperature measuring unit measures a temperature of the fluid discharged from the living body.

The pH calculating unit calculates a pH value based on the impedance of the fluid discharged from the living body, measured by the impedance measuring unit, and the temperature of the fluid discharged from the living body, measured by the temperature measuring unit. Specifically, the pH calculating unit calculates the pH value of the fluid discharged from the living body by assigning the impedance of the fluid discharged from the living body, measured by the impedance measuring unit, and the temperature of the fluid discharged from the living body, measured by the temperature measuring unit, to an equation derived in advance. The equation is, for example, $pH=(a \times T+b) \times Zhum+\delta$, where pH denotes the pH value of the fluid discharged from the living body, T denotes the temperature of the fluid discharged from the living body, Zhum denotes the impedance of the fluid discharged from the living body, and a, b, and $\delta$ denote constants. The equation is based on the fact that the impedance varies with the pH value of the fluid discharged from the living body and varies with the temperature of the fluid discharged from the living body.

The stress evaluating unit evaluates stress based on the pH value calculated by the pH calculating unit. Specifically, since the pH value of the fluid discharged from the living body varies with the stress level, the stress evaluating unit evaluates the stress corresponding to the pH value calculated by the pH calculating unit, based on the relationship between the pH value and the stress (stress point, stress determination, or the like), determined in advance.

In the inventive stress evaluation apparatus having the structure described above, the impedance measuring unit and the temperature measuring unit measure the impedance of the fluid discharged from the living body and the temperature of the fluid discharged from the living body, respectively; the pH calculating unit calculates the pH value based on the impedance and the temperature of the fluid discharged from the living body; and the stress evaluating unit evaluates the stress based on the pH value. The stress evaluation apparatus of the present invention avoids the trouble of mounting electrodes at predetermined positions on the living body and eliminates the physical discomfort of the electrodes mounted on the predetermined positions on the living body, owing to the measurement of the fluid discharged from the living body.

In addition, in the stress evaluation apparatus according to certain embodiments of the present invention, the measurement determination processing unit indicates if the impedance measuring unit does not measure the impedance of the fluid discharged from the living body and the measurement-state determination processing unit indicates if the state in which the impedance measuring unit measures the impedance of the fluid discharged from the living body is not good. Accordingly, the stress evaluation apparatus is user friendly.

Furthermore, according to certain embodiments of the stress evaluation apparatus of the present invention, the elapsed-time determination processing unit determines whether the elapsed time for the measurement exceeds one minute. The elapsed-time determination processing unit indicates if the elapsed time for the measurement exceeds one minute and causes the impedance measuring unit to perform the measurement again if the elapsed time does not exceed one minute. Accordingly, the inventive stress evaluation apparatus is user friendly and is capable of precisely acquiring sufficient measurement data.

Although the pH calculating unit in the inventive stress evaluation apparatus described above calculates the pH value in consideration of the temperature of the fluid discharged from the living body, the pH calculating unit can calculate the pH value of the fluid discharged from the living body based on the impedance of the fluid discharged from the living body, measured by the impedance measuring unit, without considering the temperature of the fluid discharged from the living body. Specifically, since the impedance varies with the pH value of the fluid discharged from the living body, in certain embodiments of the present invention the stress evaluation apparatus calculates the pH value of the fluid discharged from the living body by assigning the impedance of the fluid discharged from the living body, measured by the impedance measuring unit, to an equation, derived in advance, indicating the relationship between the pH value and the impedance. The equation is, for example, $pH = \gamma \times Zhum + \delta$ where pH denotes the pH value of the fluid discharged from the living body, $Zhum$ denotes the impedance of the frequency discharged from the living body, and $\gamma$ and $\delta$ denote constants.

A stress evaluation apparatus according to an embodiment of the present invention wherein the fluid discharged from the living body is saliva will be described in detail below.

Figure 3:
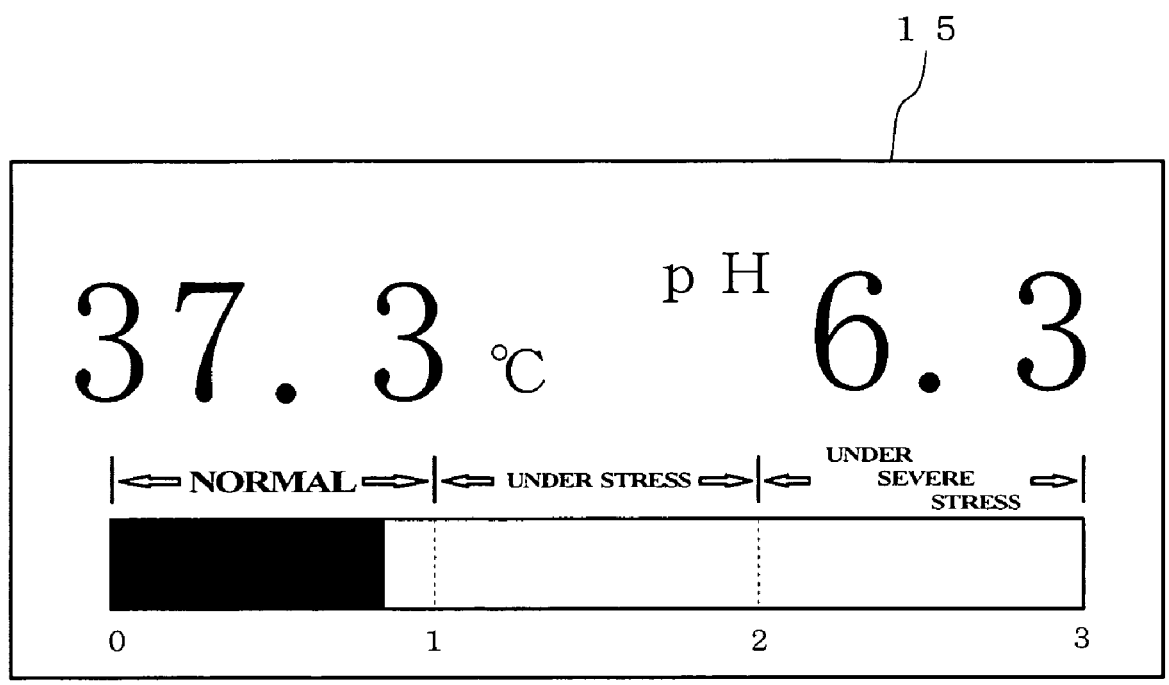
FIG. 3 shows a display screen of an indicator of a stress evaluation apparatus according to an embodiment of the present invention.

FIG. 1A is an outside view of the inventive stress evaluation apparatus in which the fluid discharged from the living body is saliva, viewed from the side put into the mouth. FIG. 1B is an outside view of the inventive stress evaluation apparatus, viewed from the side of an indicator (the front face of a holder). FIG. 2 is a block diagram of the stress evaluation apparatus. FIG. 3 shows the display screen of an indicator of the stress evaluation apparatus. FIG. 4 illustrates the stress evaluation criterion. The structure of this stress evaluation apparatus will be described with reference to FIGS. 1 to 4.

The stress evaluation apparatus according to this embodiment of the present invention has a power supply 1, a key switch 2, an oscillator 3, a band pass filter (BPF) 4, a voltage-to-current (V-I) converter 5, a reference resistance 6, a pair of current supply electrodes 7, a pair of voltage detection electrodes 8, a switch 9, an amplifier 10, an analog-to-digital (A-D) converter 11, a temperature sensor 12, an electrically erasable and programmable read only memory (EEPROM) 13, a buzzer 14, an indicator 15, and a microcontroller 16. The above components are housed in a case 17.

The case 17, which includes a bar 17a capable of being put into the mouth of the user and a holder 17b capable of being held by the user, forms the outline of the stress evaluation apparatus. The bar 17a has projections 17av formed on the periphery thereof. The projections 17av are formed so as to be in contact with the pair of current supply electrodes 7 and the pair of voltage detection electrodes 8.

The power supply 1, which is provided in the holder 17b, supplies power to each component in the electrical system of the stress evaluation apparatus.

The key switch 2 includes an ON key 2a and an OFF key 2b, which are provided on the front face of the holder 17b. When the ON key 2a is pressed, the power supply 1 supplies power to start the operation of the stress evaluation apparatus. When the OFF key 2b is pressed, the power supply 1 stops supplying the power to stop the operation of the stress evaluation apparatus.

The oscillator 3 generates an alternating-current constant voltage under the control of the microcontroller 16.

The BPF 4 passes only signals having frequencies in a certain frequency range in the alternating-current constant voltage generated in the oscillator 3.

The V-I converter 5 converts the alternating-current constant voltage passing through the BPF 4 into an alternating-current constant current, and outputs the converted the alternating-current constant current.

The reference resistance 6 is an impedance serving as a reference for compensating for the effect on the impedance measurement caused by a change in the alternating-current constant current, output from the V-I converter 5, due to a change in environment, for example, in temperature. The alternating-current constant current output from the V-I converter 5 passes through the reference resistance 6.

The pair of current supply electrodes 7 is formed around the periphery of the bar 17a at intervals. The pair of current supply electrodes 7 applies the alternating-current constant current from the reference resistance 6 to the user's saliva.

The pair of voltage detection electrodes 8 is formed around the bar 17a at intervals between the pair of current supply electrodes 7. The pair of voltage detection electrodes 8 detects a voltage generated in the saliva when the pair of current supply electrodes 7 applies the alternating-current constant current to the saliva.

The switch 9 switches a connection to either both ends of the reference resistance 6 or both electrodes of the pair of voltage detection electrodes 8.

The amplifier 10 amplifies the voltage detected when the switch 9 is switched to both ends of the reference resistance 6 or the voltage detected when the switch 9 is switched to both electrodes of the pair of voltage detection electrodes 8.

The A-D converter 11, which is in a synchronous detection mode, converts the analog voltage supplied from the amplifier 10 into a digital signal. In addition, the A-D converter 11 divides the voltage generated at both ends of the reference resistance 6 into a real part and an imaginary part and supplies the real part and the imaginary part to the microcontroller 16.

The temperature sensor 12 is provided at the tip of the bar 17a. The temperature sensor 12 detects the voltage based on the temperature of the saliva and supplies the detected temperature to the microcontroller 16. According to this embodiment, since the temperature sensor 12 measures the saliva in the mouth of the user, the temperature sensor 12 assumes the temperature of the saliva as the body temperature of the user.

The EEPROM 13 stores the result including the evaluation of the stress as history data under the control of the microcontroller 16.

The buzzer 14 is provided on the front face of the holder 17b. The buzzer 14 emits a discontinuous sound for indicating that the state in which the impedance measuring unit measures the impedance of the saliva is not good or that the elapsed time for the measurement exceeds one minute, or emits a continuous sound for indicating that the measurement is completed, under the control of the microcontroller 16.

The indicator 15 is provided on the front face of the holder 17b. As shown in detail in the screen of the indicator 15 in FIG. 3, the indicator 15 indicates a numerical value showing the measurement result of the body temperature in the upper left, indicates a numerical value showing the measurement result of the pH value of the saliva in the upper right, and indicates a horizontal bar graph showing the measurement result of the stress in the lower part, under the control of the microcontroller 16. In the horizontal bar graph, a numerical value indicating the stress point is displayed at the lower side and words indicating the stress determination are displayed at the upper side. When the stress evaluation apparatus does not measure the impedance of the saliva, the stress evaluation apparatus displays, in the indicator 15, "- - -" indicating that the impedance of the saliva has not been measured.

The microcontroller 16 includes a central processing unit (CPU), a read only memory (ROM), a random access memory (RAM), a timer, an input-output (IO) port, and so on. The microcontroller 16 performs the following processing.

i) The microcontroller 16 assigns the voltage detected when the switch 9 switches its connection to both ends of the reference resistance 6 to Equation (1) below to calculate an overall impedance.

$$Z\text{total} = p \times V\text{ref} + q \tag{1}$$

where Ztotal denotes the overall impedance, Vref denotes the voltage detected when the switch 9 switches the connection to both ends of the reference resistance 6, and p and q denote constants derived in advance by experiment.

ii) The microcontroller 16 assigns the voltage detected when the switch 9 switches its connection to both electrodes of the pair of voltage detection electrodes 8 and the voltage detected when the switch 9 switches its connection to both ends of the reference resistance 6 to Equation (2) below to calculate a temporary impedance of the saliva.

$$Z = c \times V\text{hum}/V\text{ref} + os \tag{2}$$

where Z denotes the temporary impedance of the saliva, Vhum denotes the voltage detected when the switch 9 switches the connection to both electrodes of the pair of voltage detection electrodes 8, and c and os denote constants derived in advance by experiment.

iii) The microcontroller 16 assigns the overall impedance and the temporary impedance of the saliva to Equation (3) below to calculate a contact impedance.

$$Zc = (Z\text{total} - Z)/2 \tag{3}$$

where Zc denotes the contact impedance.

iv) The microcontroller 16 assigns the contact impedance and the temporary impedance of the saliva to Equation (4) below to calculate an impedance of the saliva.

$$Z\text{hum} = (1 + k \times Zc) \times Z \tag{4}$$

where Zhum denotes the impedance of the saliva and k denotes a constant derived in advance by experiment.

v) The microcontroller 16 assigns the voltage detected by the temperature sensor 12 to Equation (5) below to calculate a temperature of the saliva (body temperature), and indicates the calculation result in the indicator 15.

$$T = \alpha \times Vt + \beta \tag{5}$$

where T denotes the temperature of the saliva (body temperature), Vt denotes the voltage based on the temperature of the saliva (body temperature), and $\alpha$ and $\beta$ denote constants derived in advance by experiment.

vi) The microcontroller 16 assigns the temperature of the saliva and the impedance of the saliva to Equation (6) below to calculate a pH value of the saliva, and indicates the calculation result in the indicator 15.

$$\text{pH} = (a \times T + b) \times Z\text{hum} + \delta \tag{6}$$

where pH denotes the pH value of the saliva, and a, b, and $\delta$ denote constant derived in advance by experiment.

vii) The microcontroller 16 evaluates stress (a stress point and stress determination) corresponding to the pH value of the saliva based on evaluation criterion shown in FIG. 4, and indicates the evaluation result in the indicator 15.

viii) The microcontroller 16 determines whether the stress evaluation apparatus has measured the impedance of the saliva, based on the determination criterion in Expression (7) below using the voltages of the real part and the imaginary part generated at both ends of the reference resistance 6, divided by the A-D converter 11. If the stress evaluation apparatus does not measure the impedance of the saliva, the microcontroller 16 indicates, in the indicator 15, that the stress evaluation apparatus has not measured the impedance of the saliva.

$$0 < \text{Imvref}/\text{Revref} < 0.25 \tag{7}$$

where Imvref denotes the voltage of the imaginary part generated at both ends of the reference resistance 6 and Revref denotes the voltage of the real part generated at both ends of the reference resistance 6.

ix) The microcontroller 16 determines whether the state in which the impedance of the saliva is measured is good, based on the determination criterion in Expression (8) below using the contact impedance and a threshold that is set in advance and that is affected by the contact impedance. If the state in which the impedance of the saliva is measured is not good, the microcontroller 16 indicates, to the buzzer 14, that the state in which the impedance of the saliva is measured is not good.

$$Zc < Zth \quad (8)$$

where Zth denotes the threshold affected by the contact impedance (constant derived in advance by experiment).

x) The microcontroller 16 measures an elapsed time of the measurement. If the state in which the impedance of the saliva is measured is not good, the microcontroller 16 determines whether the measured elapsed time for the measurement exceeds one minute. If the elapsed time for the measurement exceeds one minute, the microcontroller 16 indicates to the buzzer 14 that the elapsed time for the measurement exceeds one minute. If the elapsed time for the measurement does not exceed one minute, the microcontroller 16 causes the switch 9 to switch the connection to both ends of the reference resistance 6.

The microcontroller 16, the oscillator 3, the BPF 4, and the V-I converter 5 form a constant current generating unit 18. The switch 9, the amplifier 10, the A-D converter 11, and the microcontroller 16 form a converting unit for impedance calculation 19. The unit including the power supply 1, the constant current generating unit 18, the reference resistance 6, the pair of current supply electrodes 7, the pair of voltage detection electrodes 8, and the converting unit for impedance calculation 19 serves as the impedance measuring unit. The microcontroller 16 serves as the pH calculating unit, the stress evaluating unit, the measurement determination processing unit, the measurement-state determination processing unit, the clock unit, and the elapsed-time determination processing unit. The temperature sensor 12 and the microcontroller 16 serve as the temperature measuring unit.

Figure 5:
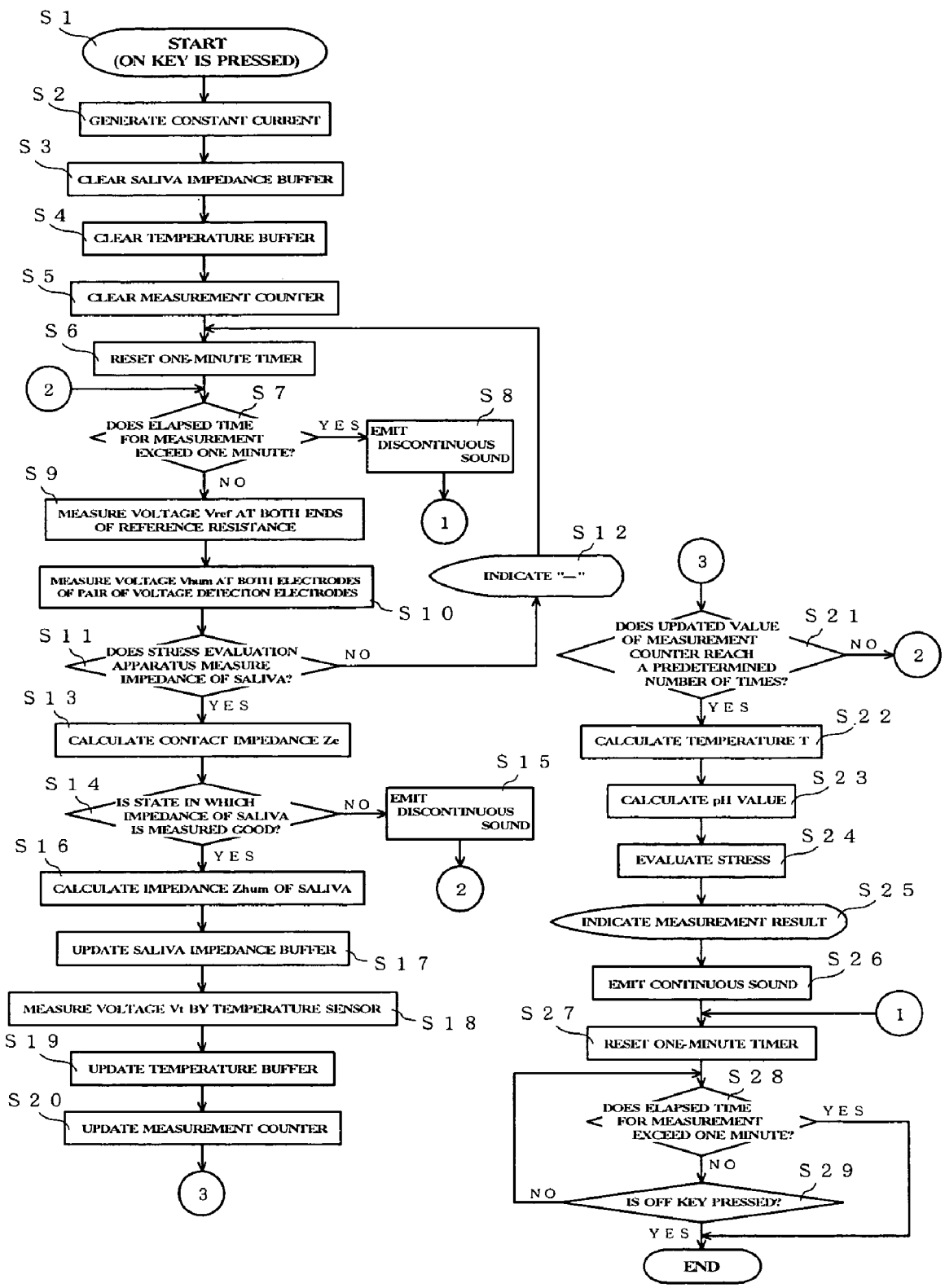
FIG. 5 is a flowchart showing a process in a stress evaluation apparatus according to an embodiment of the present invention.

A process performed by the stress evaluation apparatus of the present invention will now be described with reference to the flowchart in FIG. 5.

In Step S1, when the ON key 2a is pressed, the power supply 1 supplies power to each component in the electrical system. In Step S2, the constant current generating unit 18 generates a constant current of 100 kHz.

In Step S3, the microcontroller 16 clears an internal saliva impedance buffer. In Step S4, the microcontroller 16 clears a temperature buffer. In Step S5, the microcontroller 16 clears a measurement counter. In Step S6, the microcontroller 16 resets the timer.

In Step S7, the microcontroller 16 determines whether the elapsed time for the measurement exceeds one minute. If the elapsed time for the measurement exceeds one minute, that is, if the determination is affirmative in Step S7, then in Step S8, the buzzer 14 emits a discontinuous sound under the control of the microcontroller 16, and the process proceeds to Step S27 described below. If the elapsed time for the measurement does not exceed one minute, that is, if the determination is negative in Step S7, then in Step S9, the switch 9 switches the connection to both ends of the reference resistance 6 and measures the voltage Vref (the voltage of the real part, the voltage of the imaginary part, and the combined voltage) detected when the switch 9 switches the connection to both ends of the reference resistance 6, under the control of the microcontroller 16.

In Step S10, the switch 9 switches the connection to both electrodes of the pair of voltage detection electrodes 8 and measures the voltage Vhum detected when the switch 9 switches the connection to both electrodes of the pair of voltage detection electrodes 8, under the control of the microcontroller 16.

In Step S11, the microcontroller 16 determines whether the stress evaluation apparatus measures the impedance of the saliva, according to Expression (7) based on the relationship between the voltage of the real part and the voltage of the imaginary part, generated at both ends of the reference resistance 6.

If the determination result does not comply with Expression (7), that is, if the stress evaluation apparatus does not measure the impedance of the saliva (the determination is negative in Step S11), then in Step S12, the indicator 15 indicates "- - -" under the control of the microcontroller 16, and the process goes back to Step S6. In contrast, if the determination result complies with Expression (7), that is if the stress evaluation apparatus measures the impedance of the saliva (the determination is affirmative in Step S11), then in Step S13, the microcontroller 16 assigns the voltage detected when the switch 9 switches the connection to both ends of the reference resistance 6 to Equation (1) to calculate the overall impedance, assigns the voltage detected when the switch 9 switches the connection to both electrodes of the pair of voltage detection electrodes 8 and the voltage detected when the switch 9 switches the connection to both ends of the reference resistance 6 to Equation (2) to calculate the temporary impedance of the saliva, and assigns the overall impedance and the temporary impedance of the saliva to Equation (3) to calculate the contact impedance Zc.

In Step S14, the microcontroller 16 determines whether the state in which the impedance of the saliva is measured is good, according to Expression (8) based on the relationship between the contact impedance and the threshold that is set in advance and that is affected by the contact impedance.

If the determination result does not comply with Expression (8), that is, if the state in which the impedance of the saliva is measured is not good (the determination is negative in Step S14), then in Step S15, the buzzer 14 emits a discontinuous sound under the control of the microcontroller 16, and the process goes back to Step S7. In contrast, if the determination result complies with Expression (8), that is, if the state in which the impedance of the saliva is measured is good (the determination is affirmative in Step S14), then in Step S16, the microcontroller 16 assigns the calculated contact impedance and temporary impedance of the saliva to Equation (4) to calculate the impedance Zhum of the saliva. In Step S17, the microcontroller 16 adds the calculated impedance of the saliva to the current value of the saliva impedance buffer to accumulate and update the impedance of the saliva in the saliva impedance buffer.

In Step S18, the temperature sensor 12 measures the voltage Vt corresponding to the temperature of the saliva (body temperature) under the control of the microcontroller 16. In Step S19, the microcontroller 16 adds the measured voltage based on the temperature of the saliva (body temperature) to the current value of the temperature buffer to accumulate and update the voltage based on the temperature of the saliva (body temperature) in the temperature buffer.

In Step S20, the microcontroller 16 adds one to the current value of the measurement counter to accumulate and update the value of the measurement counter.

In Step S21, the microcontroller 16 determines whether the updated value of the measurement counter reaches a predetermined number of times (ten). The predetermined number of times is set to ten so the voltage adapted to ensure a sufficient evaluation accuracy and to minimize the measurement time, based on the impedance of the saliva and the temperature of the saliva (body temperature), can be yielded in the calculation of the temperature and the pH value.

If the value of the measurement counter does not reach the predetermined number of times (ten), that is, if the determination is negative in Step S21, the process goes back to Step S7. If the value of the measurement counter reaches the predetermined number of times (ten), that is, if the determination is affirmative in Step S21, then in Step S22, the microcontroller 16 divides the voltage based on the temperature of the saliva (body temperature), accumulated and updated in the temperature buffer, by the predetermined number of times (ten) of the measurement counter to calculate the average of the voltage based on the sampled temperature of the saliva (body temperature), and assigns the average voltage based on the temperature of the saliva (body temperature) to Equation (5) to calculate the temperature T of the saliva (body temperature).

In Step S23, the microcontroller 16 divides the impedance of the saliva accumulated and updated in the saliva impedance buffer by the predetermined number of times (ten) of the measurement counter to calculate the average of the sampled impedance of the saliva, and assigns the average impedance of the saliva and the calculated temperature of the saliva (body temperature) to Equation (6) to calculate the pH value of the saliva.

In Step S24, the microcontroller 16 evaluates a stress point and stress determination corresponding to the calculated pH value of the saliva with reference to the evaluation criterion shown in FIG. 4. For example, if the calculated pH value of the saliva is 6.3, the stress point is 0.7 and the stress determination is normal.

In Step S25, the indicator 15 indicates the evaluation of the stress, the pH value of the saliva, and the temperature of the saliva (body temperature) as the measurement result, as shown in FIG. 3. In Step S26, the buzzer 14 emits a continuous sound for indicating that the measurement is completed for a predetermined time (three seconds) under the control of the microcontroller 16.

In Step S27, the microcontroller 16 resets the timer. In Step S28, the microcontroller 16 determines whether the elapsed time for the measurement exceeds one minute. If the elapsed time for the measurement exceeds one minute, that is, if the determination is affirmative in Step S28, the power supply 1 stops supplying power to each component in the electrical system under the control of the microcontroller 16 and the process is terminated. If the elapsed time for the measurement does not exceed one minute, that is, if the determination is negative in Step S28, then in Step S29, the process determines whether the OFF key 2b is pressed.

If the OFF key 2b is not pressed, that is, if the determination is negative in Step S29, the process goes back to Step S28. If the OFF key 2b is pressed, that is, if the determination is affirmative in Step S29, the power supply 1 stops supplying power to each component in the electrical system under the control of the microcontroller 16 and the process is terminated.

The stress evaluation apparatus adapted to the case in which the fluid discharged from the living body is saliva operates in the manner described above.

Although the inventive stress evaluation apparatus measures the saliva of a living body in the embodiment described above, the stress evaluation apparatus may measure the urine of the living body by using a corresponding evaluation criterion different from the one shown in FIG. 4. In this case, the urine is directly dropped on the bar 17a or part of the bar 17a is dipped in the urine stored in a container.

Although the inventive stress evaluation apparatus measures the saliva of a living body in the embodiment described above, the stress evaluation apparatus may measure the saliva or urine of an animal other than a human being by using a corresponding evaluation criterion different from the one shown in FIG. 4.

Although the inventive stress evaluation apparatus has the temperature sensor 12 and calculates the pH value of the saliva based on the temperature of the saliva (body temperature) in the embodiment described above, in a further embodiment of the present invention the stress evaluation apparatus may not have the temperature sensor 12. In this case, the pH value of the saliva is calculated according to Equation (9) below.

$$pH = \gamma \times Zhum + \delta \quad (9)$$

where Zhum denotes the impedance of the saliva, pH denotes the pH value of the saliva, and $\gamma$ and $\delta$ denote constants derived in advance by experiment.

Figure 6A:
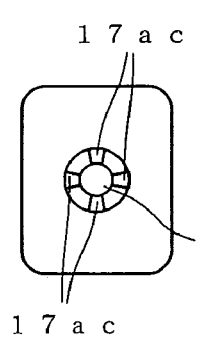
FIG. 6A is an outside view of another stress evaluation apparatus according to an embodiment of the present invention, viewed from the side put into the mouth of the living body.
Figure 6B:
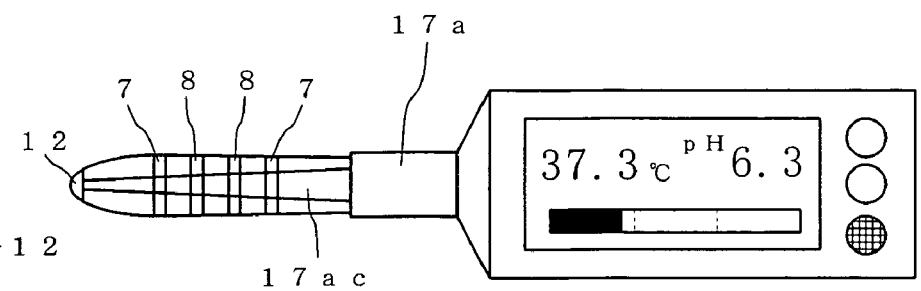
FIG. 6B is an outside view of the stress evaluation apparatus in FIG. 6A, viewed from the side of an indicator (the front face of a holder).

Although the bar 17a has the projections 17av formed on the periphery thereof in the embodiment described above, the bar 17a may have grooves 17ac, as shown in an outline view in FIG. 6. Furthermore, the grooves may be formed such that the width thereof is gradually increased from the side put into the mouth of the living body. With this structure, it is possible to prevent the saliva carried in the grooves 17ac due to the capillary action from spilling over the mouth.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only selected embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A stress evaluation apparatus comprising:
    an impedance measuring unit for measuring an impedance of a fluid discharged from a living body;
    a pH calculating unit for calculating a pH value based on the impedance of the fluid discharged from the living body; and
    a stress evaluating unit for evaluating a stress based on the pH value.

2. The stress evaluation apparatus according to claim 1, further comprising:
    a temperature measuring unit for measuring a temperature of the fluid discharged from the living body, wherein the pH calculating unit calculates the pH value based on the impedance of the fluid discharged from the living body measured by the impedance measuring unit, and the temperature of the fluid discharged from the living body measured by the temperature measuring unit.

3. The stress evaluation apparatus according to claim 1, further comprising:
a measurement determination processing unit for determining whether the impedance measuring unit has measured the impedance of the fluid discharged from the living body,
wherein if the impedance measuring unit has not measured the impedance of the fluid discharged from the living body, the measurement determination processing unit indicates that the impedance measuring unit has not measured the impedance of the fluid discharged from the living body.

4. The stress evaluation apparatus according to claim 3, wherein the impedance measuring unit comprises:
a constant current generating unit for generating an alternating-current constant current;
a reference resistance through which the alternating-current constant current generated by the constant current generating unit passes;
a pair of current supply electrodes for applying the alternating-current constant current from the reference resistance to the fluid discharged from the living body;
a pair of voltage detection electrodes for detecting a voltage generated in the fluid discharged from the living body when the pair of current supply electrodes applies the alternating-current constant current to the fluid discharged from the living body;
a switch for switching a connection to either both ends of the reference resistance or both electrodes of the pair of voltage detection electrodes; and
a converting unit for impedance calculation for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body;
wherein the converting unit divides the voltage generated at both ends of the reference resistance into a real part and an imaginary part; and
wherein the measurement determination processing unit determines whether the impedance measuring unit has measured the impedance of the fluid discharged from the living body based on the real part and the imaginary part.

5. The stress evaluation apparatus according to claim 1, further comprising:
a measurement-state determination processing unit for determining whether a state in which the impedance measuring unit measures the impedance of the fluid discharged from the living body is good;
wherein if the state in which the impedance measuring unit measures the impedance of the fluid discharged from the living body is not good, the measurement-state determination processing unit indicates that the state in which the impedance measuring unit measures the impedance of the fluid discharged from the living body is not good.

6. The stress evaluation apparatus according to claim 5, wherein the impedance measuring unit comprises:
a constant current generating unit for generating an alternating-current constant current;
a reference resistance through which the alternating-current constant current generated by the constant current generating unit passes;
a pair of current supply electrodes for applying the alternating-current constant current from the reference resistance to the fluid discharged from the living body;
a pair of voltage detection electrodes for detecting a voltage generated in the fluid discharged from the living body when the pair of current supply electrodes applies the alternating-current constant current to the fluid discharged from the living body;
a switch for switching a connection to either both ends of the reference resistance or both electrodes of the pair of voltage detection electrodes; and
a converting unit for impedance calculation, for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body;
wherein the measurement-state determination processing unit determines whether the state in which the impedance measuring unit measures the impedance of the fluid discharged from the living body is good based on the contact impedance calculated by the converting unit and a predetermined threshold that is affected by the contact impedance.

7. The stress evaluation apparatus according to claim 5, further comprising:
a clock unit for measuring an elapsed time of measurement; and
an elapsed-time determination processing unit for determining whether the elapsed time for the measurement measured by the clock unit exceeds one minute if the measurement-state determination processing unit determines that the state in which the impedance measuring unit measures the impedance of the fluid discharged from the living body is not good,
wherein the elapsed-time determination processing unit indicates that the elapsed time for the measurement exceeds one minute if the elapsed time for the measurement exceeds one minute, and causes the impedance measuring unit to perform the measurement if the elapsed time for the measurement does not exceed one minute.

8. The stress evaluation apparatus according to claim 1, wherein the impedance measuring unit comprises:
   a constant current generating unit for generating an alternating-current constant current;
   a reference resistance through which the alternating-current constant current generated by the constant current generating unit passes;
   a pair of current supply electrodes for applying the alternating-current constant current from the reference resistance to the fluid discharged from the living body;
   a pair of voltage detection electrodes for detecting a voltage generated in the fluid discharged from the living body when the pair of current supply electrodes applies the alternating-current constant current to the fluid discharged from the living body;
   a switch for switching a connection to either both ends of the reference resistance or both electrodes of the pair of voltage detection electrodes; and
   a converting unit for impedance calculation for calculating an overall impedance based on the voltage detected when the switch switches the connection to both ends of the reference resistance, calculating a temporary impedance of the fluid discharged from the living body based on the voltage detected when the switch switches the connection to both electrodes of the pair of voltage detection electrodes and the voltage detected when the switch switches the connection to both ends of the reference resistance, calculating a contact impedance based on the calculated overall impedance and temporary impedance of the fluid discharged from the living body, and calculating the impedance of the fluid discharged from the living body based on the contact impedance and the temporary impedance of the fluid discharged from the living body.

9. The stress evaluation apparatus according to any of claims 1 to 8,
   wherein the fluid discharged from the living body is saliva.

10. The stress evaluation apparatus according to any of claims 1 to 8,
    wherein the fluid discharged from the living body is urine.

11. The stress evaluation apparatus according to claim 8,
    wherein the fluid discharged from the living body is saliva,
    wherein the stress evaluation apparatus has a bar for insertion into the mouth of the living body,
    wherein the bar has the pair of current supply electrodes, the pair of voltage detection electrodes, and projections in contact with the pair of current supply electrodes and the pair of voltage detection electrodes, and
    wherein the pair of current supply electrodes, the pair of voltage detection electrodes, and the projections are formed on the periphery of the bar.

12. The stress evaluation apparatus according to claim 8,
    wherein the fluid discharged from the living body is saliva,
    wherein the stress evaluation apparatus has a bar for insertion into the mouth of the living body,
    wherein the bar has the pair of current supply electrodes, the pair of voltage detection electrodes, and grooves in contact with the pair of current supply electrodes and the pair of voltage detection electrodes, and
    wherein the pair of current supply electrodes, the pair of voltage detection electrodes, and the grooves are formed on the periphery of the bar.

13. The stress evaluation apparatus according to claim 12,
    wherein the grooves are formed such that the width thereof is gradually increased from a side of the bar inserted into the mouth of the living body.

* * * * *